(12) United States Patent  
Bonathan et al.

(10) Patent No.: US 8,567,230 B2
(45) Date of Patent: Oct. 29, 2013

(54) IMPACT TEST FIXTURE (75) Inventors: Darren G. Bonathan, Wayne, MI (US); Ronald J. Rothley, Highland, MI (US)

(73) Assignee: Nissan North America, Inc., Franklin, TN (US)

( * ) Notice: Subject to any disclaimer, the term of this patent is extended or adjusted under 35 U.S.C. 154(b) by 148 days.

(21) Appl. No.: 13/214,755

(22) Filed: Aug. 22, 2011

(65) Prior Publication Data

US 2013/0047700 A1 Feb. 28, 2013

(51) Int. Cl.
*G01M 7/00* (2006.01)

(52) U.S. Cl.
USPC ........................................................ 73/12.04

(58) Field of Classification Search
USPC ........................................................ 73/12.04
See application file for complete search history.

(56) References Cited

U.S. PATENT DOCUMENTS

| | | | |
|---|---|---|---|
| 1,461,787 A | 7/1923 | Stebbins | |
| 2,518,073 A | 8/1950 | Sargent | |
| 3,444,629 A * | 5/1969 | Ward | 434/375 |
| 3,645,016 A * | 2/1972 | Wiegand | 434/375 |
| 3,715,814 A * | 2/1973 | Wiegand | 434/375 |
| 3,905,134 A * | 9/1975 | Greenleaf et al. | 434/375 |
| 5,003,811 A * | 4/1991 | Shannon et al. | 73/12.14 |
| 6,595,087 B2 | 7/2003 | Whalen et al. | |
| 6,955,250 B2 | 10/2005 | Kreider et al. | |
| 6,990,845 B2 * | 1/2006 | Voon et al. | 73/12.14 |
| 2005/0124730 A1 | 6/2005 | Yamazaki | |

FOREIGN PATENT DOCUMENTS

WO    8505425    12/1985

\* cited by examiner

*Primary Examiner* — Lisa Caputo
*Assistant Examiner* — Octavia D. Hollington
(74) *Attorney, Agent, or Firm* — Young, Basile, Hanlon & MacFarlane, P.C.

(57) ABSTRACT

An impact test fixture includes an arm, a testing actuator connected to the arm, and an impactor supported by the testing actuator. The testing actuator is actuatable to propel the impactor at a predetermined speed with respect to the arm. A mass dampener is associated with the arm for reducing deflection of the arm as a result of actuation of the testing actuator.

22 Claims, 7 Drawing Sheets

IMPACT TEST FIXTURE

TECHNICAL FIELD

The disclosure relates to the field of motor vehicle safety testing, and more particularly, to an impact test fixture for motor vehicle safety testing.

BACKGROUND

In many countries, motor vehicles are required to be rigorously tested for compliance with safety standards. In the United States, the required testing is specified by the Federal Motor Vehicle Safety Standards (FMVSS).

Many of these tests involve simulating the impact of an object with respect to a vehicle. The target area on the vehicle is typically specified by the test. Typically, the target area is small, and the impact force that is applied to the vehicle must be controlled with a high degree of accuracy and precision to ensure that the impact force is applied within the target zone.

SUMMARY

Impact test fixtures are disclosed herein.

One aspect of the embodiments taught herein is an impact test fixture that includes an arm, a testing actuator that is connected to the arm, and an impactor that is supported by the testing actuator. The testing actuator is actuatable to propel the impactor at a predetermined speed with respect to the arm. A mass dampener is associated with the arm for reducing deflection of the arm as a result of actuation of the testing actuator.

Another aspect of the embodiments taught herein is an impact test fixture that includes an arm, a testing actuator that is connected to the arm, and an impactor that is supported by the testing actuator. The testing actuator is actuatable to propel the impactor at a predetermined speed with respect to the arm. A mass dampener is associated with the arm for reducing deflection of the arm as a result of actuation of the testing actuator. The mass dampener includes a vessel that is fixed in place with respect to the arm. The vessel has a plurality of shot pellets disposed therein.

Another aspect of the embodiments taught herein is an impact test fixture that includes an arm and a base structure for supporting the arm. The base structure includes a three-axis positioning system for moving the arm in an x-direction, a y-direction, and a z-direction. A testing actuator is connected to the arm. An impactor is supported by the testing actuator. The testing actuator is actuatable to propel the impactor at a predetermined speed with respect to the arm. A mass dampener is associated with the arm for reducing deflection of the arm as a result of actuation of the testing actuator.

BRIEF DESCRIPTION OF THE DRAWINGS

The description herein makes reference to the accompanying drawings wherein like reference numerals refer to like parts throughout the several views, and wherein.

DETAILED DESCRIPTION

One impact test that is required by certain safety standards involves simulating a collision between a vehicle and an object, such as an external object striking the hood of the vehicle. This test is conducted by impacting the hood of the vehicle with a semi-spherical impactor that includes sensors that measure the force of the impact. An actuator launches the projectile toward the hood with great force. The actuator is supported by a test fixture. When the projectile is launched by the actuator, it was determined that a force of approximately 300 pounds is applied to the test fixture by the actuator. The force applied to the test fixture can induce oscillations within the test fixture, thereby causing the impactor to land outside of the target area. In one test, the impactor was filmed using high speed video. Review of the video revealed that the force of the actuator was inducing large deflections and oscillations in the fixture.

Figure 1:
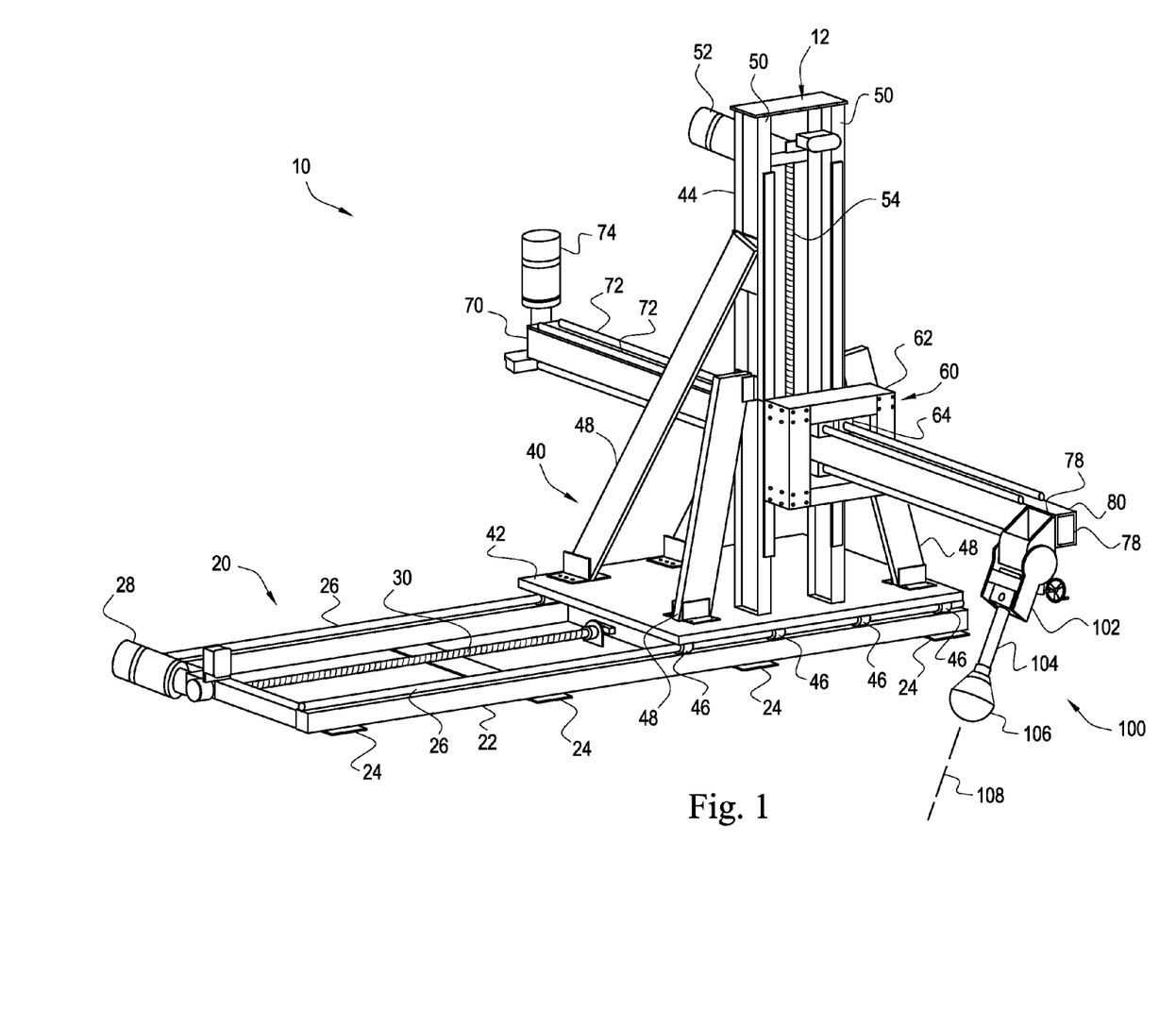
FIG. 1 is a perspective view of an impact test fixture including an impactor assembly according to a first example.
Figure 2:
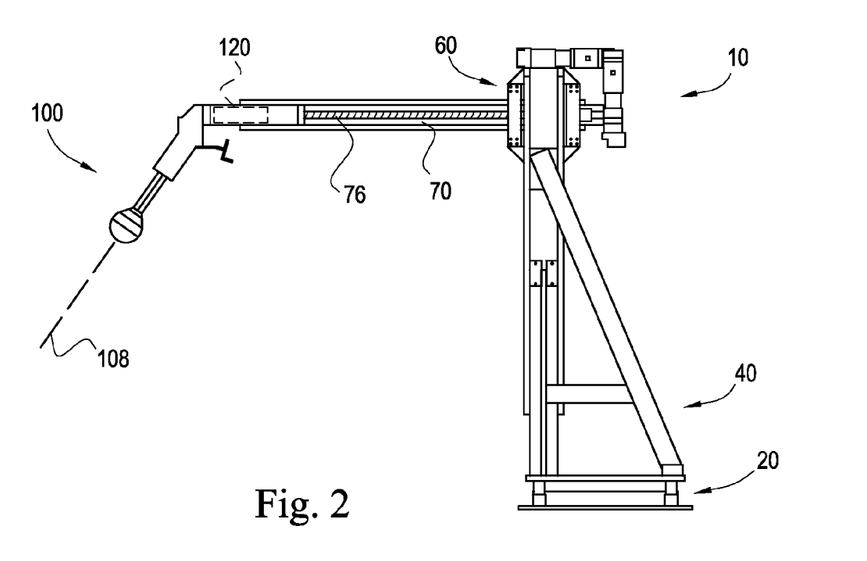
FIG. 2 is an end view of the impact test fixture.
Figure 3:
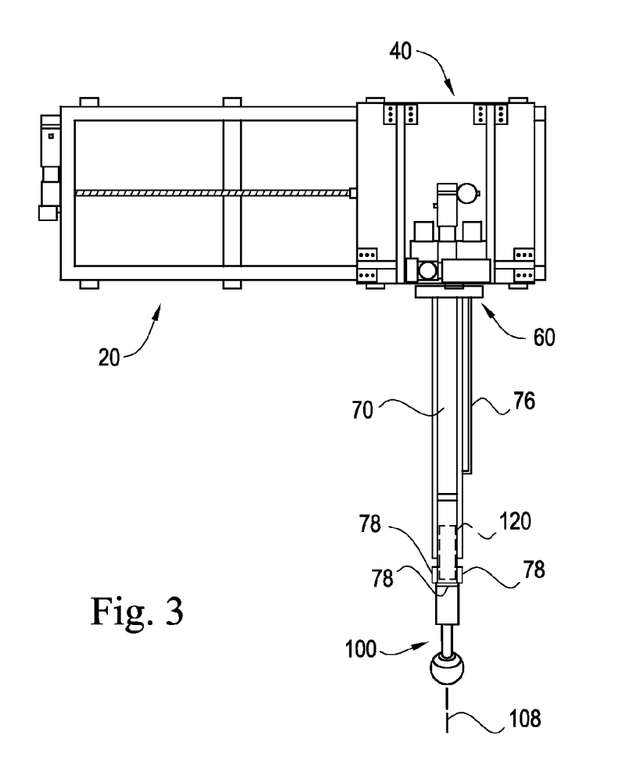
FIG. 3 is a top view of the impact test fixture.

FIGS. 1-3 show an impact test fixture 10 having an impactor assembly 100 according to a first example. The impact test fixture 10 includes a base structure 12 that incorporates a three-axis positioning system in the form of an X-stage 20, a Z-stage 40, and a Y-stage 60. The impact test fixture 10 also includes an arm 70 that is supported by the Y-stage 60. The impactor assembly 100 is supported by the arm 70. The X-stage 20, the Z-stage 40, and the Y-stage 60 provide for movement of the impactor assembly 100 and an X direction, a Y direction, and a Z direction, respectively. In this example, the impactor assembly 100 is capable of being positioned over a 6 foot range in each of the X direction, Y direction, and the Z direction. However, the impact test fixture 10 could be constructed to provide any desired range of travel for the impactor assembly 100. Furthermore, the arm 70 could be supported by base structures other than a base structure that incorporates a three-axis positioning system.

The X-stage 20 includes a base frame 22 that is connectable to a floor (not shown) by means such as bolts (not shown) that extend through mounting plates 24 and are connected to the base frame 22. Linear rails 26 are connected to the base frame 22 and extend in the X direction.

The Z-stage 40 is supported by the linear rails 26 of the X-stage 20 for movement in the X direction with respect to the base frame 22 of the X-stage 20. In order to move the Z-stage 40 with respect to the X-stage 20, the X-stage 20 includes positioning means such as a motor 28 and a lead screw 30. The motor 28 is operable to turn the lead screw 30. The lead screw 30 is connected to the Z-stage 40 such that rotation of the lead screw 30 causes linear movement of the Z-stage 40 along the linear rails 26. The motor 28 and the lead screw 30 are examples of a suitable positioning means for moving the Z-stage 40 with respect to the X-stage 20. It should be understood, however, that at any positioning means now known or later developed could be utilized.

The Z-stage 40 includes a carriage 42 and a tower frame 44 that extends upward with respect to the carriage 42. The carriage 42 is a substantially planar member that is supported by the linear rails 26 of the X-stage 20. For example, bearing elements 46 such as slide blocks or other suitable types of linear bearings can be provided on the carriage 42 for sliding engagement with the linear rails 26 of the X-stage 20.

The tower frame 44 is rigidly mounted to the carriage 42. Bracing members 48 may be connected to the carriage 42 and the tower frame 44 in order to stabilize the tower frame 44 with respect to the carriage 42. The Y-stage 60 is supported by the tower frame 44 of the Z-stage 40. Linear rails 50 extend along the tower frame 44 in a generally upright orientation. The linear rails 50 can be substantially vertical.

The Y-stage 60 is movable along the linear rails 50 of the Z-stage 40 for movement in the Z direction with respect to the tower frame 44 of the Z-stage 40. In order to move the Y-stage 60 with respect to the Z-stage 40, the Z-stage 40 includes positioning means such as a motor 52 and a lead screw 54. The motor 52 is operable to turn the lead screw 54. The lead screw 54 is connected to the Y-stage 60 such that rotation of the lead screw 54 causes linear movement of the Y-stage 60 in the Z direction along the linear rails 50 of the Z-stage 40. The motor 52 and the lead screw 54 are examples of a suitable positioning means for moving the Y-stage 60 with respect to the Z-stage 40. It should be understood, however, that any positioning means now known or later developed could be utilized.

The Y-stage 60 includes a carriage 62 that is connected to the linear rails 50 of the Z-stage 40. Linear bearings, slide blocks, or other suitable means (not shown) can be utilized to slidably connect the carriage 62 of the Y-stage 60 the linear rails 50 of the Z-stage 40.

The arm 70 is slidably connected to the carriage 62 of the Y-stage 60 for sliding movement of the arm 70 in the Y direction with respect to the carriage 62 of the Y-stage 60. Linear rails 72 are connected to the arm 70. The linear rails 72 are slidably connected to linear bearings 64 or other suitable connecting structures that are attached to the carriage 62 of the Y-stage 60.

In order to move the arm 70 in the Y direction with respect to the carriage 62 of the Y-stage 60, a positioning motor 74 and a lead screw 76 are connected to the arm 70. The positioning motor 74 is operable to turn the lead screw 76. The lead screw 76 is connected to the Y-stage 60 such that rotation of the lead screw 76 causes linear movement of the arm 70 in the Y direction by sliding motion of the linear rails 72 of the arm 70 along the linear bearings 64 of the carriage 62 of the Y-stage 60. The positioning motor 74 and the lead screw 76 are examples of a suitable positioning means for moving the arm 70 with respect to the Y-stage 60. It should be understood, however, that any positioning means now known or later developed could be utilized.

The impactor assembly 100 is connected to one of a plurality of mounting plates 78 that are positioned at an end portion 80 of the arm 70, which is a distal end of the arm 70 relative to the base structure 12. A first mounting configuration of the impactor assembly 100 is shown in FIG. 1, and a second mounting configuration of the impactor assembly 100 is shown in FIGS. 2-3.

The impactor assembly 100 includes a mounting structure 102, a testing actuator 104, and an impactor 106. The mounting structure 102 is directly connected to one of the mounting plates 78 of the arm 70. The mounting structure 102 can be adjustable. For example, the mounting structure 102 can allow for adjustment of the angle of the testing actuator 104 in one or more angular degrees of freedom, thereby adjusting the angle of a firing axis 108 of the testing actuator 104.

The testing actuator 104 is connected to the arm 70 by the mounting structure 102.

The impactor 106 is supported by the testing actuator 104. The impactor 106 is a structure that is configured to strike another structure. The impactor 106 can be a device that is configured in accordance with vehicle testing standards, such as FMVSS 201.

The testing actuator 104 is actuatable to propel the impactor 106 at a predetermined speed with respect to the arm 70. For example, the testing actuator 104 can be a pneumatic actuator that is capable of propelling the impactor 106 with high speed and force over a short range of motion along the firing axis 108. Other types of actuators could be utilized as the testing actuator 104, such as hydraulic actuators, electrical actuators, or any other suitable type of device for imparting high speed, high force linear motion now known or later developed.

Figure 4A:
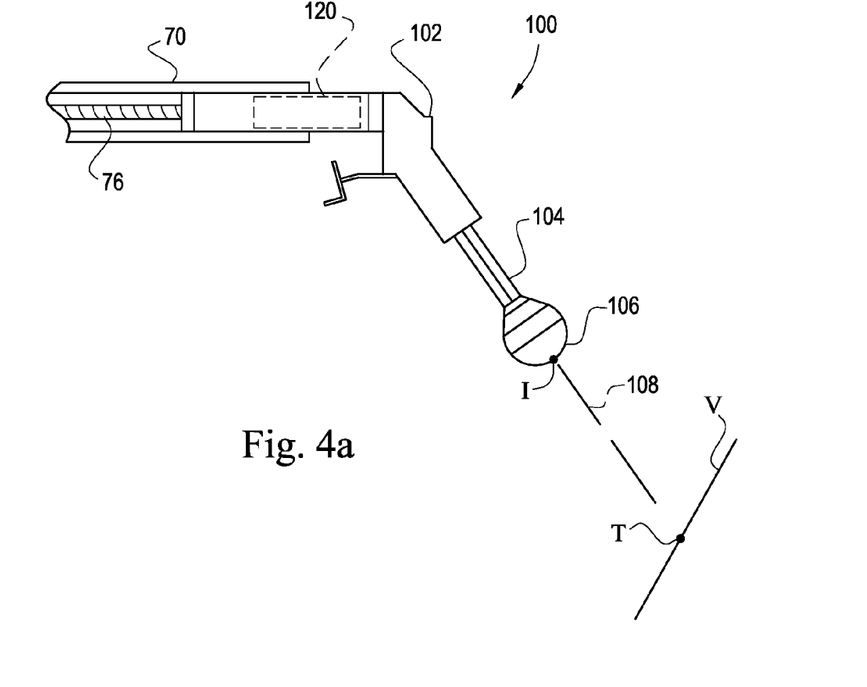
FIG. 4A-4D are side views depicting actuation of an impactor assembly according to a first example.
Figure 4B:
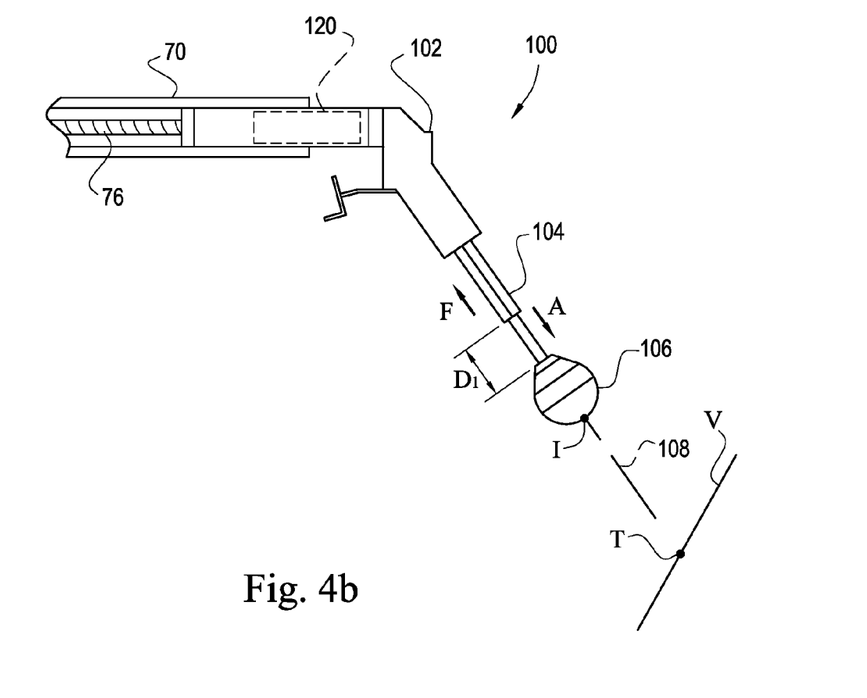
Figure 4C:
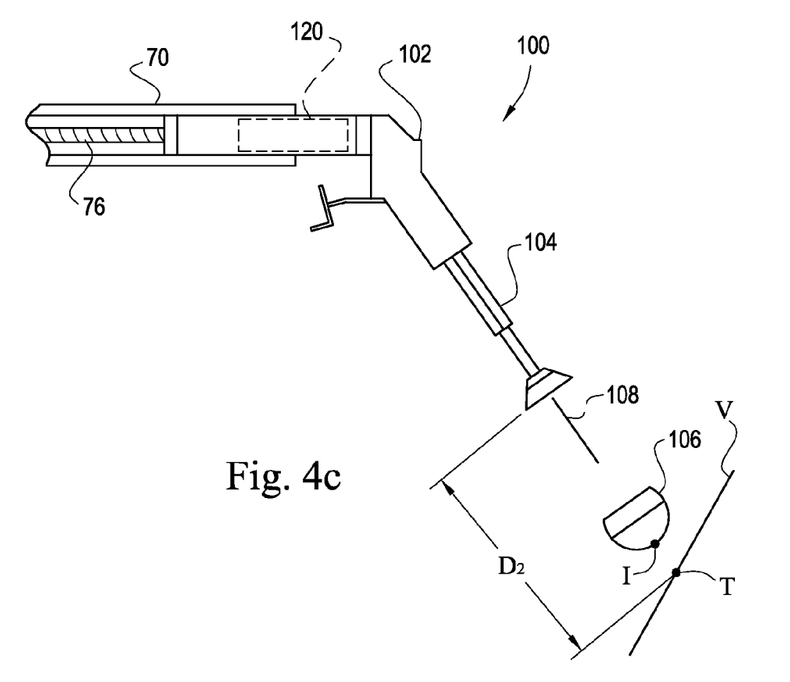
Figure 4D:
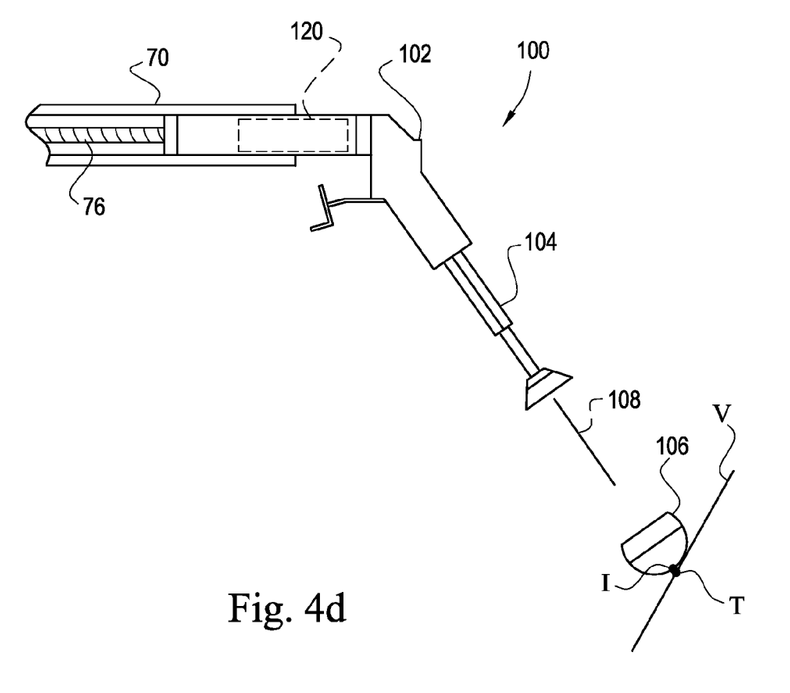

During actuation of the testing actuator 104, the testing actuator 104 propels the impactor 106 along the firing axis 108, and the impactor 106 separates from the testing actuator 104 prior to contacting the vehicle V, as shown in FIGS. 4A-4D. Prior to actuation, the testing actuator 104 is disposed in a retracted position (FIG. 4A) Upon actuation of the testing actuator 104, the impactor 106 is pushed toward the vehicle V along the firing axis 108 for a first distance D1 (FIG. 4B), which defines an extended position for the testing actuator 104, and the impactor 106 is then released to travel the remaining distance D2 (FIG. 4C) until the impactor 106 contacts the vehicle V (FIG. 4D). The impactor 106 can remain connected to the mounting structure 102, or another part of the impactor assembly 100 or the impact test fixture 10 via a tether (not shown), as long as the impactor 106 is free to travel the entire distance between the actuator 104 and the vehicle V along the firing axis 108. Alternatively, the impactor 106 can be released to travel the entire distance between the actuator 104 and the vehicle V. Also, or remain connected to a portion of the actuator 104 until the impactor 106 contacts the vehicle V. Regardless of the form of actuation the testing actuator 104 is aimed such that an impact point I on the impactor 106 is aligned along the firing axis 108 to make contact with a target point T on the vehicle upon impact after actuation.

The testing actuator 104 is connected to the end portion 80 of the arm 70, which is distal or cantilevered from the base structure 12. By applying an actuation force A to deploy the impactor 106 towards the vehicle V, a reactive force F can be applied to the distal end 80 of the arm 70, which can cause deflection and oscilation of the arm 70 with respect to the base structure 12 (FIG. 4B). If the arm is deflected during actuation, the firing axis 108 may become unaligned with the target point T, causing the impact point I to miss the target point T when impacting the vehicle V.

Figure 5:
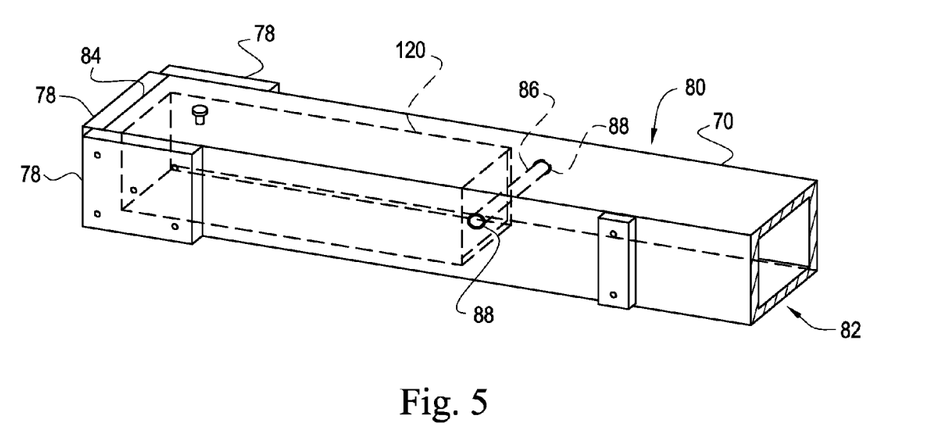
FIG. 5 is a perspective view showing an end portion of an arm of the impact test fixture.

As shown in FIG. 5, the arm 70 is an elongate member, and can have a substantially square cross-section in a direction that is substantially transverse to the arm 70. The arm 70 is tubular, and thus defines an interior 82 that is substantially hollow.

A mass dampener 120 is associated with the arm 70 for reducing deflections and oscillations of the arm 70 as a result of actuation of the testing actuator 104. The mass dampener 120 is a device that is configured to reduce oscillations in the arm 70 in response to actuation of the testing actuator 104. In this example, the mass dampener 120 is disposed within the arm 70, by disposition of the mass dampener 120 in the interior 82 of the arm 70.

The mass dampener 120 includes a vessel in the form of tube 122 that is disposed within the arm 70. The tube 122 can be fabricated from aluminum.

The tube 122 is fixed in place with respect to the arm 70. For example, the mass dampener 120 can be fixed in place with respect to the arm 70 by disposition of the mass dampener 120 between an end wall 84 of the arm 70 and a pin 86 that is spaced from the end wall 84 by the mass dampener 120. The pin 86 extends transverse to the arm 70 and can be seated in apertures 88 that are formed in the arm 70. Other structures can be used to fix the mass dampener 120 in place with respect to the arm 70. As an example, mechanical fasteners can be used to directly connect the mass dampener 120 to the arm 70.

Figure 6:
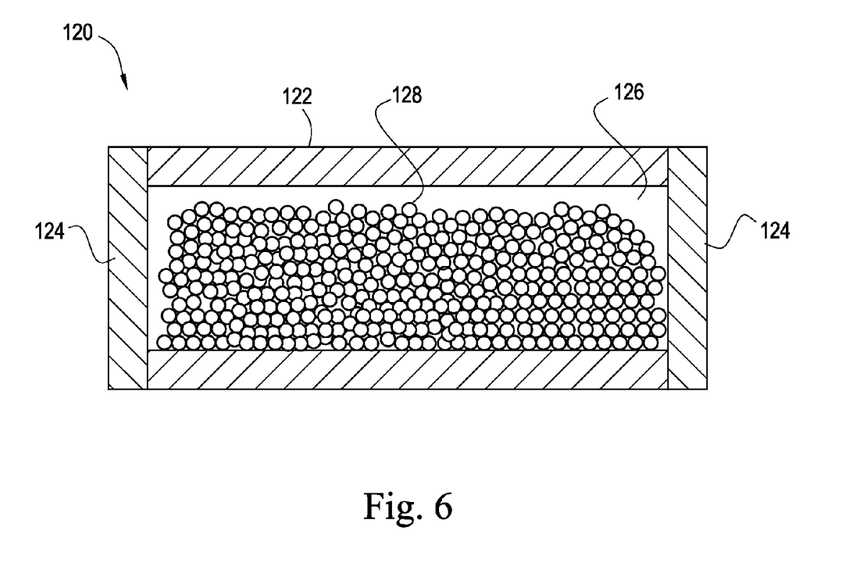
FIG. 6 is a side cross-section view of a mass dampener.

As shown in FIG. 6, the tube 122 includes or is connected to closed ends 124 that define an interior 126 for the mass dampener 120 that is substantially enclosed. The interior 126 of the mass dampener 120 has a ballast material disposed therein. The ballast material is moveable within the interior 126. Thus, the volume of the interior 126 of the mass dampener 120 is greater than a volume of the ballast material, such that the ballast material does not completely fill the interior 126 of the mass dampener 120. In this example, the ballast material is in the form of a plurality of shot pellets 128 that are disposed within the interior 126 of the mass dampener 120. The shot pellets 128 have a volume that is approximately 90 percent or less of the volume of the interior 126 of the mass dampener 120. Although the ballast material is shown as a plurality of shot pellets 128, a fluid such as water may also be used as the ballast material.

In operation, the impact test fixture 10 is utilized to perform an impact test. The impactor assembly 100 is positioned with respect to a target using the X-stage 20, the Z-stage 40 and the Y-stage 60 of the impact test fixture 10. The testing actuator 104 is actuated, which causes the testing actuator 104 to propel the impactor 106 with respect to the arm 70, such as at a predetermined speed. Upon actuation of the testing actuator 104, the impactor 106 travels along the firing axis 108 and strikes the target. Sensors within the impactor 106 record the forces applied to the impactor 106. The mass dampener 120 reduces deflection and oscillation of the arm 70 during actuation of the testing actuator 104, thereby allowing the target to be struck consistently.

In one test, the impact test fixture was fitted with a mass dampener having approximately 90 pounds of lead shot. High speed video showed that deflections were maintained under 10 mm, with little oscillation. Additional tests were repeated with no more than 2 mm of variation.

Figure 7:
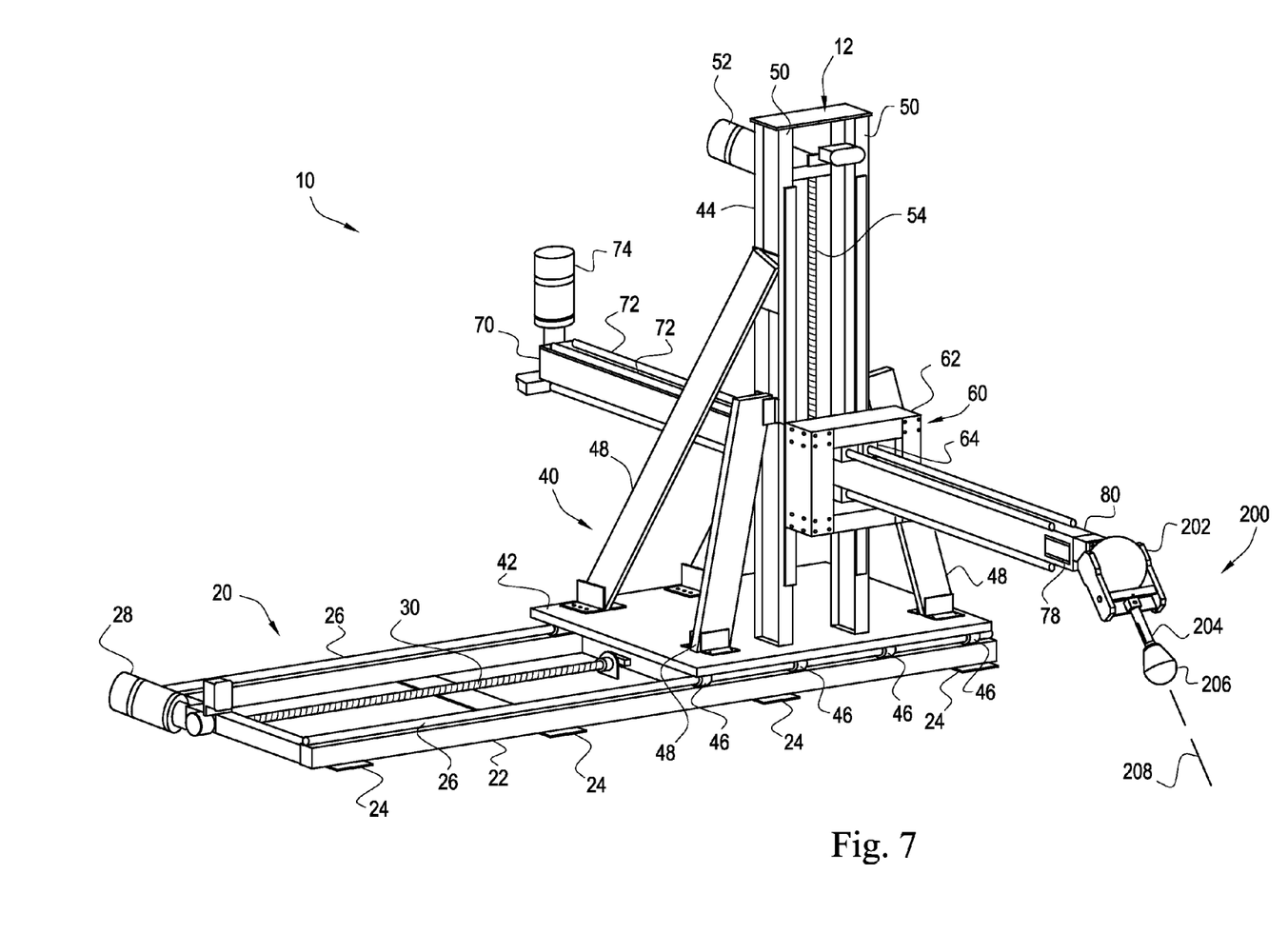
FIG. 7 is a perspective view of an impact test fixture including an impactor assembly according to a second example.

In FIG. 7, the impact test fixture 10 has an impactor assembly 200 according to a second example. The impact test fixture 10 is as described in connection with FIGS. 1-3. In this example, however, a mass dampener 220 is incorporated as part of the impactor assembly 200, in addition to or in place of the mass dampener 120.

The impactor assembly 200 includes a mounting structure 202, a testing actuator 204, and an impactor 206. The mounting structure 202 is directly connected to one of the mounting plates 78 of the arm 70. The mounting structure 202 supports the testing actuator 204 and the impactor 206, which is connected to the testing actuator 204. In all relevant details, the testing actuator 204 and the impactor 206 are identical to the testing actuator 104 and the impactor 106, as previously described.

Figure 8:
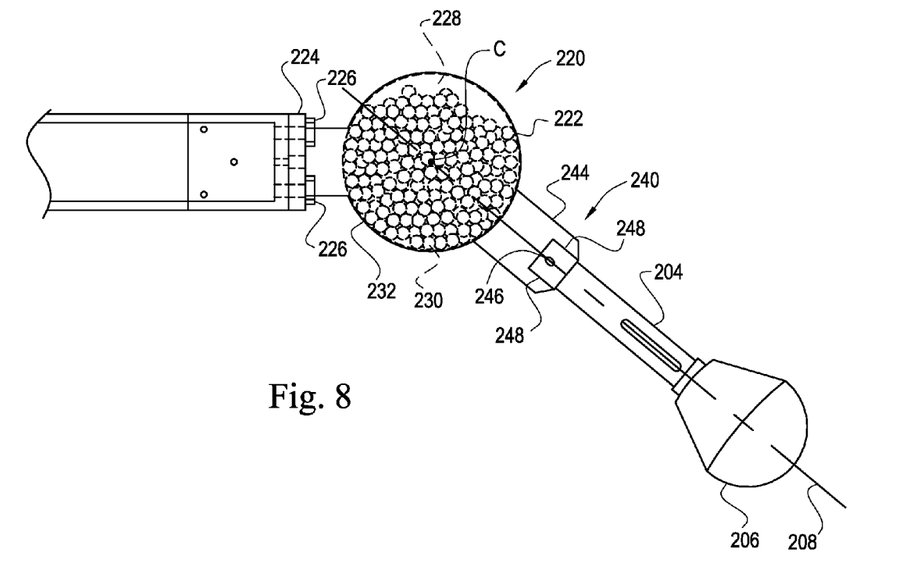
FIG. 8 is a side view of an impactor assembly according to the second example.
Figure 9:
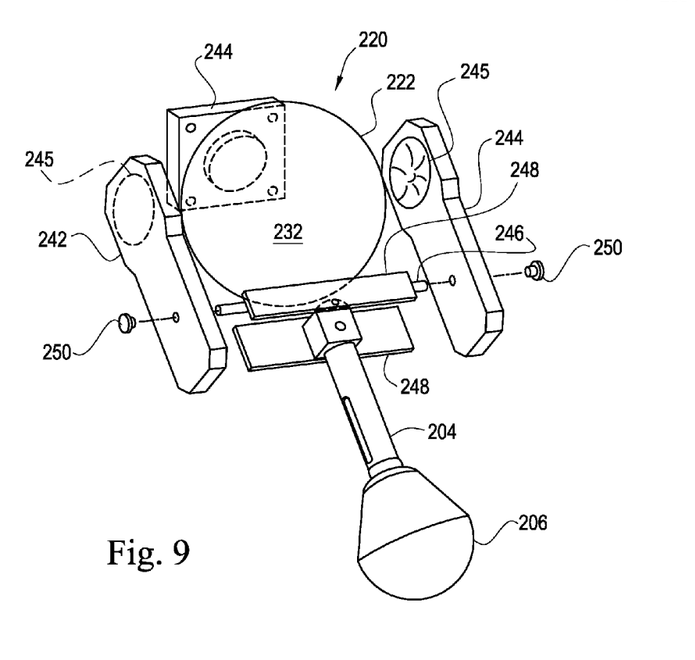
FIG. 9 is an exploded perspective view of the impactor assembly according to the second example.

The mounting structure 202 includes the mass dampener 220, as shown in FIGS. 8-9. The mass dampener 220 includes a substantially spherical vessel 222. Thus, the substantially spherical vessel 222 is a portion of the mounting structure 202, which that connects the testing actuator 204 to the arm.

As used herein, the term "substantially spherical" means that the element need not define a complete sphere, and that deviations from a perfect spherical shape are contemplated. For example, only a partial of a sphere could be defined by a substantially spherical element. A substantial sphere could have a continuous or discontinuous surface. Slots, grooves, blanks or holes could be formed in the discontinuous surface of a substantial sphere. Facets could be formed on a substantial sphere, and thus, a substantial sphere could include a polyhedron having a sufficient number of faces to render its shape roughly spherical.

The substantially spherical vessel 222 is rigidly connected to a mounting member 224. The mounting member 224 is rigidly connected to one of the mounting plates 78 of the arm 70, such as by bolts 226. Thus, the substantially spherical vessel 222 is rigidly connected to the arm 70 by the mounting member 224.

The substantially spherical vessel 222 defines an interior 228 that is substantially hollow. The interior 228 of the substantially spherical vessel 222 has a ballast material disposed therein. The ballast material is moveable within the interior 228. Thus, the volume of the interior 228 of the mass dampener 220 is greater than a volume of the ballast material, such that the ballast material does not completely fill the interior 228 of the mass dampener 220. In this example, the ballast material is in the form of a plurality of shot pellets 230 that are disposed within the interior 228 of the mass dampener 220. The shot pellets 230 have a volume that is approximately 90 percent or less of the volume of the interior 228 of the mass dampener 220.

The substantially spherical vessel 222 of the mass dampener 220 defines a substantially spherical exterior surface 232. The substantially spherical exterior surface 232 is a surface that is at least a portion of shape that approximates a sphere, and need not be a complete and perfect sphere, as explained with regard to the substantially spherical vessel 222. Instead, it is sufficient that the substantially spherical exterior surface 232 be sufficiently spherical to allow a rolling motion of the substantially spherical exterior surface 232 with respect to other objects, or of other objects with respect to the substantially spherical exterior surface 232.

The mounting structure 202 includes a bracket assembly 240 that is adapted to be clamped to the substantially spherical exterior surface 232 of the substantially spherical vessel 222. This allows the bracket assembly 240 to define an adjustable position with respect to the substantially spherical vessel 222. The adjustable position of the bracket assembly 240 allows adjustment of a firing axis 208 of the impactor 206 to be adjusted in three angular degrees of freedom. This is accomplished by clamping the bracket assembly 240 to the substantially spherical exterior surface 232 in any desired orientation.

The bracket assembly 240 includes a first clamping arm 242 and a second clamping arm 244 that are disposed opposite one another, and include arcuate surfaces 245, which are indentations formed in the clamping arms 242, 244 that are complementary in shape to the substantially spherical exterior surface 232 of the substantially spherical vessel 222. The arcuate surfaces 245 of the clamping arms 242, 244 are engageable with the substantially spherical exterior surface 232 of the substantially spherical vessel 222 to fix the position of the bracket assembly 240 with respect to the substantially spherical vessel 222.

The first clamping arm 242 and the second clamping arm 244 are connected to one another by a connecting rod 246 and a pair of cross braces 248. The cross braces 248 are connected to the testing actuator 204. The connecting rod 246 extends from the first clamping arm 242 to the second clamping arm 244. A pair of fasteners 250 is associated with the connecting rod 246, and each of the fasteners 250 is disposed at an opposite end of the connecting rod 246. When the fasteners 250 are tightened with respect to the connecting rod 246, the clamping force applied to the substantially spherical vessel 222 increases. When the fasteners 250 are fully engaged, the bracket assembly 240 is fixed in position with respect to the substantially spherical vessel 222. When the fasteners 250 are at least partially disengaged, the position of the bracket assembly 240 is adjustable with respect to the substantially spherical vessel 222.

The adjustable relationship of the bracket assembly 240 with respect to the substantially spherical vessel 222 is such that the firing axis 208 of the testing actuator 204 extends through the mass dampener 220 regardless of the angular position of the bracket assembly 240 with respect to the substantially spherical vessel 222. This enhances the dampening effect that is provided by the mass dampener 220 when the testing actuator 204 is actuated.

To achieve a maximum dampening effect, the firing axes 108 and 208 should extend as close as possible to a center of mass C of the respective mass dampeners 120 and 220. Preferably, as shown in FIG. 7, the firing axis 208 passes directly through the center of mass C of the ballast material filling the interior 228 of the substantially spherical vessel 222.

Use of the impact test fixture 10 in combination with the impactor assembly 200 occurs in the same manner as previously described.

The foregoing description relates to what is presently considered to be the most practical embodiment. It is to be understood, however, that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. An impact test fixture, comprising:
   a base;
   an arm having a distal end being distal from the base, the arm being coupled to the base such that the arm is selectively movable and fixable relative to the base;
   a testing actuator connected to the arm at the distal end;
   an impactor supported by the testing actuator, wherein the testing actuator is actuatable to propel the impactor away from the distal end of the arm while the arm is fixed relative to the base; and
   a mass dampener associated with the arm for reducing deflection of the distal end of the arm relative to the base as a result of actuation of the testing actuator while the arm is fixed relative to the base.

2. The impact test fixture of claim 1, wherein the mass dampener is disposed within the arm.

3. The impact test fixture of claim 1, wherein the mass dampener includes a tube that is disposed within the arm.

4. The impact test fixture of claim 1, further comprising:
   a mounting structure coupling the testing actuator to the distal end of the arm, and the mass dampener is a portion of the mounting structure.

5. The impact test fixture of claim 4, wherein at least a portion of the mass dampener defines a substantially spherical surface.

6. The impact test fixture of claim 5, wherein the mounting structure includes a bracket that is adapted to be clamped to the substantially spherical surface to selectively adjust a position of the bracket with respect to the mass dampener.

7. The impact test fixture of claim 1, wherein the mass dampener includes a vessel having a ballast material disposed therein.

8. The impact test fixture of claim 7, wherein a volume of the vessel is greater than a volume of the ballast material.

9. The impact test fixture of claim 1, wherein the mass dampener is fixed to a distal end of the arm.

10. The impact test fixture of claim 1, further comprising:
    a positioning structure configured to selectively move the arm relative to the base along three transverse axes.

11. An impact test fixture, comprising:
    a base structure;
    an arm supported by the base structure and having a distal end that is distal from the base structure;
    a testing actuator connected to the arm at the distal end;
    an impactor supported by the testing actuator, wherein the testing actuator is actuatable to propel the impactor away from the distal end of the arm; and
    a mass dampener fixed to the arm at the distal end for reducing deflection of the arm as a result of actuation of the testing actuator.

12. The impact test fixture of claim 11, wherein the mass dampener includes a vessel with a ballast material disposed therein.

13. The impact test fixture of claim 11, wherein the mass dampener is disposed within the arm.

14. The impact test fixture of claim 11, further comprising:
    a mounting structure coupling the testing actuator to the distal end of the arm, and the mass dampener is a portion of the mounting structure.

15. The impact test fixture of claim 14, wherein at least a portion of the mass dampener defines a substantially spherical surface, and the mounting structure includes a bracket that is adapted to be clamped to the substantially spherical surface to selectively adjust a position of the bracket with respect to the mass dampener.

16. An impact test fixture, comprising:
    an arm;
    a testing actuator connected to the arm;
    an impactor supported by the testing actuator, wherein the testing actuator is actuatable to propel the impactor away from the arm; and
    a mass dampener disposed within the arm for reducing deflection of the arm as a result of actuation of the testing actuator.

17. The impact test fixture of claim 16 wherein the actuator propels the impactor along a firing axis that extends proximate to a center of mass of the mass dampener.

18. The impact test fixture of claim 16, wherein the mass dampener includes a vessel having a ballast material disposed therein.

19. An impact test fixture, comprising:
    an arm;
    a testing actuator connected to the arm;
    an impactor supported by the testing actuator, wherein the testing actuator is actuatable to propel the impactor away from the arm; and
    a mounting structure connecting the testing actuator to the arm and including a mass dampener having a substantially spherical surface.

20. The impact test fixture of claim 19 wherein the actuator propels the impactor along a firing axis that extends through a center of mass of the mass dampener.

21. The impact test fixture of claim 19, wherein the mounting structure includes a bracket that is connected to the testing actuator and adapted to be clamped to the substantially spherical surface to selectively adjust a position of the bracket with respect to the mass dampener.

22. The impact test fixture of claim 19, wherein the mass dampener includes a vessel having a ballast material disposed therein.

* * * * *